United States Patent [19]

Wilcox et al.

[11] Patent Number: 5,745,243
[45] Date of Patent: Apr. 28, 1998

[54] PHOTOMETER APPARATUS

[75] Inventors: Steven Wilcox; Don S. Goldman, both of Folsom, Calif.

[73] Assignee: Optical Solutions, Inc., Folsom, Calif.

[21] Appl. No.: 749,419

[22] Filed: Nov. 15, 1996

[51] Int. Cl.$^6$ .................................................. G01N 21/27
[52] U.S. Cl. ........................ 356/419; 250/339.12; 250/373
[58] Field of Search ........................ 356/402, 406, 356/407, 411, 414, 416, 419; 250/226, 373, 339.12

[56] References Cited

U.S. PATENT DOCUMENTS

| | | | |
|---|---|---|---|
| 3,532,434 | 10/1970 | Jones, Jr. et al. | 356/407 |
| 3,941,487 | 3/1976 | Ehret et al. | 356/411 |
| 4,637,730 | 1/1987 | Ponstingl et al. | 356/411 |
| 4,657,398 | 4/1987 | Brunsting | 356/418 |

*Primary Examiner*—F. L. Evans
*Attorney, Agent, or Firm*—Bielen, Peterson & Lampe

[57] ABSTRACT

A photometer for measuring electromagnetic radiation absorption of a sample utilizing a source of the electromagnetic radiation. Electromagnetic radiation is conducted from the source, to a sample sensor, and is passed through the sample utilizing a sample cell. The electromagnetic radiation is then directed to a detection system which determines absorbance of electromagnetic radiation by the sample at the sample cell. The detection system includes a beam splitter which receives the electromagnetic radiation and outputs first and second beams. A first detector having a first wavelength filter and a second detector having a second wavelength filter receives the two beams from the splitters. One detector may be employed to produce a reference signal. The remaining detector or detectors produce an output signal which is a representation of a characteristic, such as absorbance of the sample. The output signals are operated on by a reference signal, and converted into a measurement absorbance.

11 Claims, 3 Drawing Sheets

PHOTOMETER APPARATUS

BACKGROUND OF THE INVENTION

The present invention relates to a novel and useful photometer for measuring electromagnetic radiation properties modified by a sample.

Photometers have been used in many situations to determine the measurement of a species in a liquid body. Such measurements are based on the commonly assumed Beer's Law relationship. That is to say, the concentration of the species at one wavelength is proportional to absorbance of electromagnetic radiation for a given path through the sample and at a particular wavelength. Simple photometers are capable of making spectrophotometric measurements by directing electromagnetic radiation through a cell containing a fluid sample and measuring the characteristics of the light transmitted through the cell. Normally, the light transmitted through the tube containing the fluid is compared to a neutral or control fluid to ascertain absorbance.

It has also been determined that spectrophotometers or photometers, such as those employing filter wheels, may be employed to measure light transmitted through a sample at different wavelengths. Unfortunately, such measurements sequentially examine different wavelengths and may produce inconsistent results due to the time differences in taking such measurements. Such problems are especially acute when the fluid is flowing through the cell at a particular rate of speed. In other words, a sample volume has flowed passed the cell between measurements at first and second wavelengths.

U.S. Pat. No. 4,657,398 depicts a photometer measuring device which simultaneously measures light passing through a fluid sample using multiple light paths and a circularly variable filter. Separate detectors are employed for analysis. However, such circularly variable filter comprises a moving part which is susceptible to inconsistencies. In addition, changing the filters in the circularly variable filter is a difficult task, requiring time and effort to accomplish should a large number of wavelengths be selected for analysis of the sample.

U.S. Pat. No. 4,637,730 depicts an absorptiometer in which light is collimated into two light beams, one beam being used as a reference signal, and the other beam being transmitted through the liquid to be measured. The reference beam is transmitted by a fiber optic cable to a reference photo cell for comparison with the beam transmitted through the sample. The power supply for the light source is regulated to a constant energy through a feedback circuit. The signals are passed to log amplifiers and compared. The results are displayed digitally.

A photometer for measuring absorbance of electromagnetic radiation through a sample simultaneously at multiple wavelengths which is compact, reliable, having no moving parts, and versatile would be a notable advance in the field of chemical analyses.

SUMMARY OF THE INVENTION

In accordance with the present invention a novel and useful photometer for measuring electromagnetic radiation transmitted through a sample is herein provided.

The photometer of the present invention employs a source of electromagnetic radiation which may be visible light, ultraviolet radiation, infrared radiation, and the like. In certain cases, the source of electromagnetic radiation may be a broad wavelength source. The source of electromagnetic radiation may include stabilizing means for maintaining a predetermined intensity of the source throughout the measuring process. Such stabilizing means may include appropriate feedback circuitry to achieve this result.

Sensing means is also included in the present invention for transmitting the electromagnetic radiation from the source through the sample. The sensing means receives electromagnetic radiation from the source via one conduit means, which may be a fiber optic cable. In addition, the sensing means may take the form of a flow cell, cuvette cell, fiber optic probe, and the like. For example, in a flow cell, the liquid sample is passed therethrough while the electromagnetic radiation from the source is directed through the sample, to produce an electromagnetic signal.

Detecting means is employed for converting the electromagnetic signal to an electrical signal representing the absorbance by the sample of the electromagnetic radiation from the source. The detecting means provides the capability of making such determination at multiple wavelengths at the same time. Second conduit means is employed to direct electromagnetic radiation from the sensing means to the detecting means. In certain cases, a collimating lens may be employed prior to the transmitted electromagnetic radiation reaching the detecting means. The detecting means includes at least one beam splitter and, preferably, a multiplicity of beam splitters in tandem. One beam splitter receives the electromagnetic radiation passed through the sensing means and the second conduit means. The beam splitter outputs first and second beams in angular configuration to one another. The first beam passes to a first detector having a first wavelength filter, while the second beam passes to a second detector having a second wavelength filter. In certain cases, the second beam may be passed to a second beam splitter which, again, produces third and fourth beams, each of which passes to a separate detector, which may include a lens and filter. Any of the detectors employed in the detecting means may include a particular narrow band wavelength filter. Thus, the electromagnetic radiation from the source, sent through the sample is analyzed substantially instantaneously by multiple detectors. Any of the detectors may be of particular type, such as Silicon, InGaAs, Germanium, and the like. Such detectors may be mixed and/or matched in the present photometer. One of the beams from any of the beam splitters may be employed for a reference signal, commensurate with beam strength parameters.

Certain portions of the detecting means may be temperature stabilized by a thermostat. Such thermostating of the detection means produces a very stable measuring device with low photometric and wavelengths drifts. In addition, each of the wavelength filters of each detector is easily replaceable with a filter having a different wavelength band. Lenses may also be employed with each of the particular wavelength filters used with each of the detectors.

The electrical signals from each of the detectors are then processed when analyzing to produce a refined signal which may be easily quantified and displayed visually.

It may apparent that a novel and useful photometer has been described above.

It is therefore an object of the present invention to provide a photometer which is compact in size and very stable in measuring absorbance simultaneously in a sample at multiple wavelengths from a broad band electromagnetic radiation source.

Another object of the present invention is to provide a photometer which is compact in size and may be easily transported for use to different locations.

Yet another object of the present invention is to provide a photometer which has no moving parts.

A further object of the present invention is to provide a photometer which includes the ability of measuring absorbance of electromagnetic radiation from a source at multiple wavelengths, simultaneously.

A further object of the present invention is to provide a photometer which is constructed with a plurality of particular wavelengths filters used in conjunction with the multiplicity of detectors, and further provides easy replacement and interchangability of such filters to vary the particular wavelength of electromagnetic radiation used for analysis.

Another object of the present invention is to provide a photometer which is safely and remotely useable even in environments subject to explosions.

Yet another object of the present invention is to provide a photometer which employs an optically stabilized light source to maintain a constant intensity of electromagnetic radiation over a certain time period.

Another object of the present invention is to provide a photometer which employs a single beam through a sample and which obtains a reference signal from the same beam.

Another object of the present invention is to provide a photometer which is especially useful in determining concentration of sample of a fluid traveling through the cell.

Yet another object of the present invention is to provide a photometer which may employ detectors of different types to simultaneously measure absorbance of a sample at different wavelengths of electromagnetic radiation, e.g., visible light, near infrared radiation, ultraviolet radiation, and the like.

The invention possesses other objects and advantages especially as concerns particular characteristics and features thereof which will become apparent as the specification continues.

Figure 1:
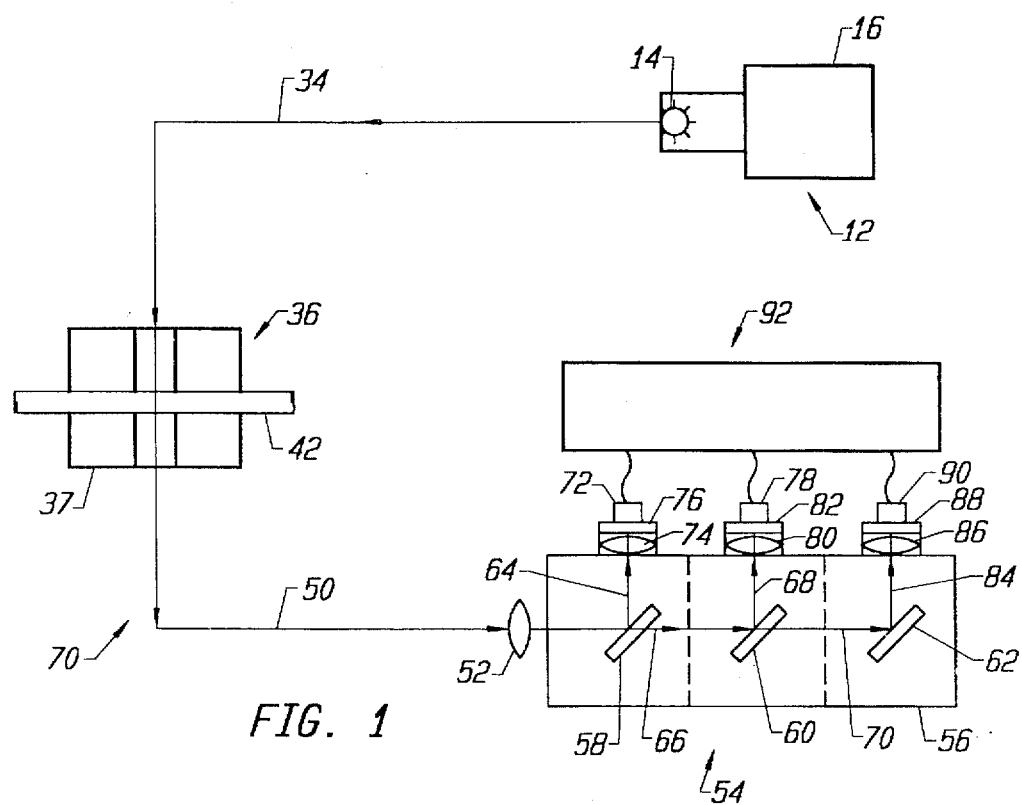
FIG. 1 is a schematic representation of the photometer of the present invention.

For a better understanding, reference is made to the following detailed description of the preferred embodiments thereof which should be taken in conjunction with the prior described drawings.

DETAILED DESCRIPTION OF THE PREFERRED EMBODIMENTS

Various aspects of the present invention will evolve from the following detailed description of the preferred embodiments thereof which should be taken in conjunction with the prior described drawings.

The invention as a whole is shown in the drawings by reference character 10. Photometer 10 includes as one of its elements, a source 12 of electromagnetic radiation. Source 12 may possess a broad wavelength band source of light, such as tungsten lamp 14. However, it should be understood that any source of electromagnetic radiation in the visible or non-visible spectrum may be employed in this regard. For example, ultraviolet and infrared wavelengths are particularly useful for certain analyses employing photometer 10. Lamp 14 includes stabilizing means 16 for maintaining a predetermined intensity of source 12.

Figure 2:
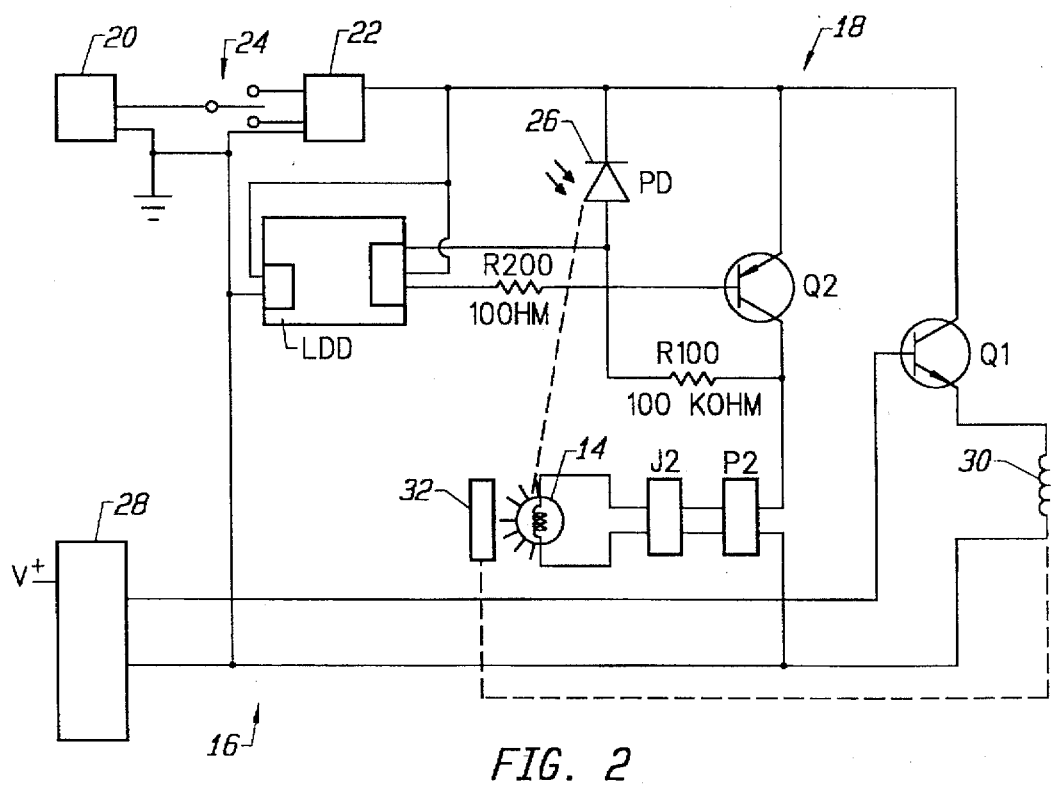
FIG. 2 is a circuit diagram showing stabilization of the source of electromagnetic radiation used with the photometer of the present invention.

Turning to FIG. 2, it may be observed that stabilizing means 16 is shown in specific detail. Optically stabilized light source 14 includes a feedback circuit 18 which essentially controls the voltage to lamp 14, minimizing intensity variations over time. The power source 20 is switched to connector 22 through single pole switch 24. Photo diode, PD 26 optically connects to lamp 14, indicated by dash line on FIG. 2. Photo diode, PD 26 regulates a current to laser diode driver, LDD, a commercially available product. LDD, in turn, sends a signal to the base of transistor Q2 which serves as a lamp driver. It should be noted that the current collector of driver Q2 provides energy to lamp 14 via connector J2, P2. Connector block 28 receives a control voltage (V+) which, in turn, passes to the base of solenoid and driver Q1, a PNP transistor. Optional solenoid 30, in turn, is capable of moving mask 32 in front of lamp 14 for specialty measuring techniques, i.e., to measure dark characteristics of photometer 10. Feedback damping resistor R1 detects analog hysteresis in the system and limits isolations therein. This damping effect is particularly helpful when the stabilizing means 16 is in its start-up mode.

Figure 4:
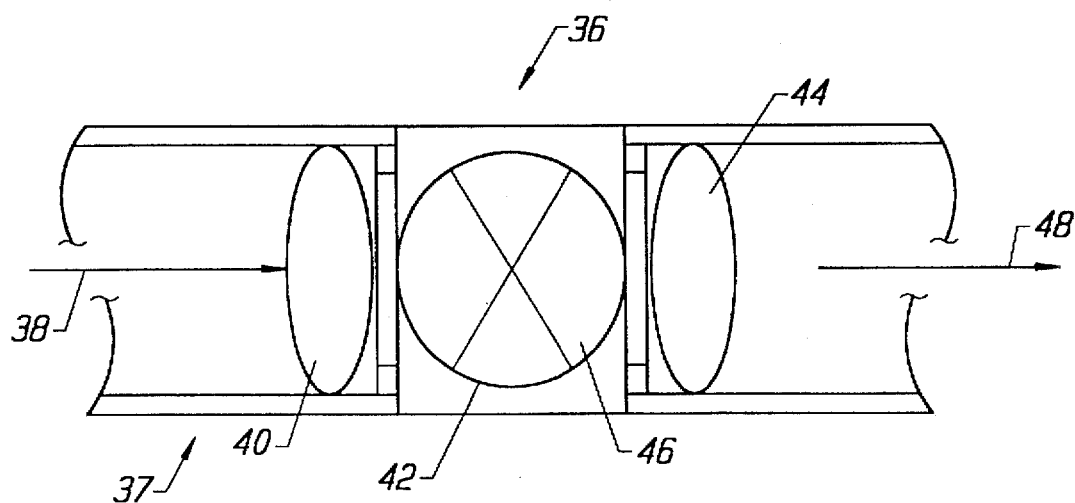
FIG. 4 is a schematic sectional view of the flow cell employed in the preferred embodiment of the present invention.

Photometer 10 also includes as one of its elements, conduit means 34 for transmitting electromagnetic radiation from source 12 to sensing means 36. Conduit means 34 may be a fiber optic cable or any suitable conduit of electromagnetic radiation. Sensing means 36, in FIGS. 1 and 4 is essentially depicted in the form of a flow cell 37. Flow cell 37 is diagramed in FIG. 4. However, sensing means 36 may take the form of a cuvette cell, fiber-optic probe, reflectance device, such as a reflectance probe and the like. For example, a planar wavelength internal reflectance probe manufactured by Optical Solutions, Inc. of Folsom, Calif. would suffice in this regard. That is to say, directional arrow 38 depicts electromagnetic radiation emitting from lamp 14 and carried via conduit means 34. Optional lens 40 collimates the electromagnetic radiation from conduit means 34 through or to a sample cell 42 which is substantially transparent to such electromagnetic radiation. Lens 44 again focuses the electromagnetic radiation after interaction or modification by sample 46 within flow cell 42, producing an electromagnetic signal. Directional arrow 48 represents electromagnetic radiation which has interacted with sample 46 and is capable of revealing a property of the sample such as the absorbance, fluorescence, transmission, turbidity, optical density, and the like. Absorbance is known to be directly related to concentration of a particular sample 46 within cell 42 (Beers Law).

Returning to FIG. 1, conduit means 50 directs the electromagnetic radiation represented by directional arrow 38 to collimating lens 52. Electromagnetic radiation exiting collimating lens 52 is directed to detecting means 54.

Detecting means 54 converts the electromagnetic signal from sensing means 36 to electrical signals. Detecting means 54 utilizes a housing 56 which is shown schematically on FIG. 1. Housing 56 includes beam splitters 58 and 60, as well as mirror 62. Beam splitter 58 reflects a first beam 64 and transmits a second beam 66. Second beam 66 passes to beam splitter 60 which reflects a third beam 68 and transmits a fourth beam 70. First beam 64 passes to a first detector 72 having a lens 74 and a wavelength filter 76. The wavelength filter 76 may be of any bandwidth suitable for the analysis of sample 46 within cell 42. Likewise, third beam 68 reflected from beam splitter 60 passes to second detector 78 after passing through lens 80 and second wavelength filter 82. Second filter 82 may possess the same or a different wavelength band than the first wavelength filter 76. Finally, fourth beam 70 is reflected from mirror 62 into a fifth beam 84 which passes through lens 86 and third wavelength filter 88, to third detector 90. It should be noted that the lens-filter combinations 74, 76; 80, 82; 86, 88 may be reversed from the positions shown in FIG. 1. For example, lens 74 may lie immediately adjacent detector 72. Detectors 72, 78 and 90 each produce an output signal which is passed to analyzing means 92 for quantification and display. Any one of the detectors, 72, 78 or 90 may be used as a reference signal in the present system. Generally, where absorbance is measured in the present photometer 10, the reference signal is chosen at a wavelength where sample 46 exhibits minimal absorbance or change in absorbance. In fact, although a pair of beam splitters 58 and 60 are shown in FIG. 1, further beam splitters may be employed in tandem with beam splitters 58 and 60 prior to mirror 62 in the present system. Of course, the use of multiple beam splitters corresponds to the intensity of the light entering detecting means 54. It should be noted that filters 76, 82 and 88 are easily interchanged in the present system. Thus, the absorbances of sample 46 may be analyzed at a multiplicity of particular wavelengths at the same time.

Figure 3:
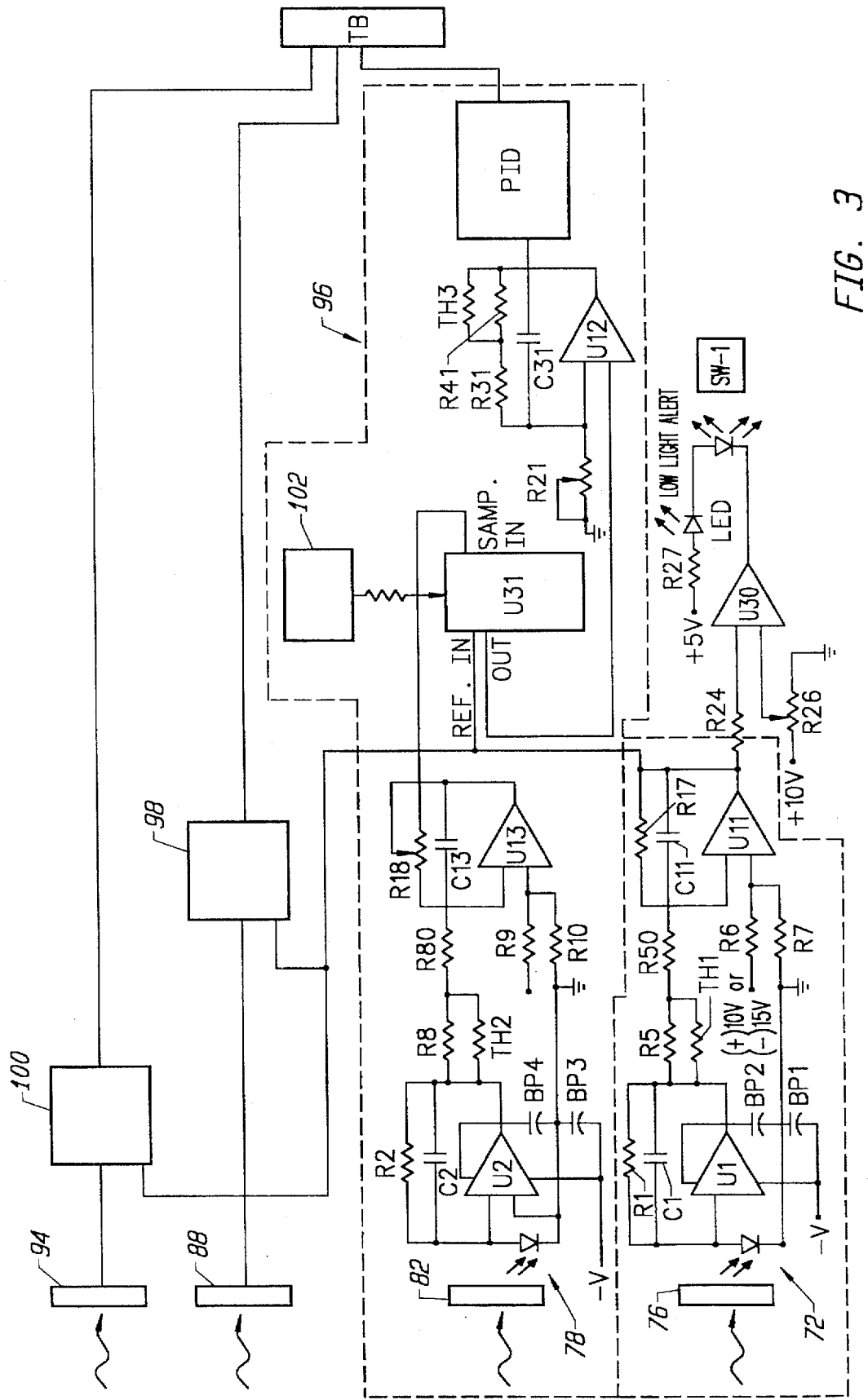
FIG. 3 is a circuit diagram indicating the analyzing means employed in the detecting means of the present invention

Turning to FIG. 3, analyzing means 92 is shown in conjunction with wavelength filters 76, 82 and 88, and an additional wavelength filter 94, not shown in FIG. 1. The circuitry associated with filter 76 is employed in FIG. 3 as a reference signal. The circuitry employed in relation to filter 82 processes light from source 14 for the purpose of analysis. Analysis circuits 98 and 100 are essentially similar to circuit 96 used in conjunction with wavelength filter 82. Returning to FIG. 1, optical filters 76 and 82, associated detectors 72 and 78 feed the transduced electrical signals into the input of high gain transimpedance amplifiers U1 and U2. Detectors 72 and 78 may take the form of Silicon, Germanium, and InGaAs, graded or extended InGaAs types, and the like. The reference signal from U1 is amplified by U11 and fed to one side of differential log amplifier U31. The sample detector signal from detector 78 is amplified by U13. U30 in combination with an optically coupled switch determines low light condition of the reference signal. Resistor pairs R6, R7, R9 and R10 offset and correct the signal prior to being sent to differential log amplifier U31. The output of U13 is compared to the output of U11, the reference signal i.e., (log-reference) minus (log-sample). The output of differential log amplifier U31 is gain and temperature corrected by a post amplifier U12. This signal is sent to the proportional integrating differentiating controller, PID, for display, signal conditioning, scale conversion, and/or translation. Terminal block (TB) provides user access to analyzing means 92. Gain changes on the input to differential log amplifier U31 will show as an offset (zero adjust) resistor by R18. After passing through differential log-amplifier U31, gain resistor R21 provides for scale adjustment, which is initially set to absorbance units. The temperature of U31 is thermostatically controlled by heater 102.

The following is a list of components used in the circuit of FIG. 3.

TABLE OF COMPONENTS

| | | | |
|---|---|---|---|
| 1. | Filters 76, 82, 88, 94 | CVI Laser | Albuquerque, NM |
| 2. | OP AMPS U1, and U2, U11, U12, U13 | Burr Brown | Phoenix, AZ |
| 3. | D.L.A. U31 | Analog Devices | Norwood, MASS |
| 4. | P.I.D. | Sixth Sense | Williston, UT |
| 5. | Thermistors TH1, TH2 and TH3, 10, Kohm | Keystone Therm | St. Marys, PA |
| 6. | Comparitor U30 | National Semi Conductor | Santa Clara, CA |
| 7. | Detectors 72, 78, 90 | Epitaxx (InGaAs) EG&G (silicon) | Princeton, NJ Santa Clara, CA |
| 8. | Beam Splitters 58, 60 | Edmunds Scientific | Barrington, NJ |
| 9. | Lamp 14 | Welch Allen | Skaneateles Falls NY |
| 10. | Flow Cell 37 | C.I.C. Photonics | Albuquerque, NM |

Resistors:

| | | |
|---|---|---|
| R1 | 1–500 mohm | Phillips, Sunnyvale, CA |
| R2 | 1–500 mohm | Phillips, Sunnyvale, CA |
| R5 | 10 Kohm | Phillips, Sunnyvale, CA |
| R50 | 49.9 Kohm | Phillips, Sunnyvale, CA |
| R6 | 10 ohm | Phillips, Sunnyvale, CA |
| R7 | 10–100 Kohm | Phillips, Sunnyvale, CA |
| R8 | 10 Kohm | Phillips, Sunnyvale, CA |
| R80 | 49.9 Kohm | Phillips, Sunnyvale, CA |
| R9 | 10–100 Kohm | Phillips, Sunnyvale, CA |
| R10 | 10 Kohm | Phillips, Sunnyvale, CA |
| R17 | 20–100 Kohm | Phillips, Sunnyvale, CA |
| R18 | 0–100 Kohm | Bourns, Riverside, CA |
| R21 | 0–5 Kohm | Bourns, Riverside, CA |
| R24 | 3 Kohm | Phillips, Sunnyvale, CA |
| R26 | 0–100 Kohm | Bourns, Riverside, CA |
| R27 | 200 Ohm | Phillips, Sunnyvale, CA |
| R31 | 10–30 Kohm | Phillips, Sunnyvale, CA |
| R41 | 10 Kohm | Phillips, Sunnyvale, CA |

Capacitors:

| | | |
|---|---|---|
| C1 | Open | |
| C2 | Open | |
| BP1, BP2, BP3 and BP4 | 1.0 µf | Murata, Smyrna, GA |
| C11 and C12 | 10 pf | Murata, Smyrna, GA |
| C13 | Open µ | |
| C31 | 0.1 µf | Murata, Smyrna, GA |

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

The following example is meant to further illustrate the invention, but is not deemed to limit the invention in any manner.

EXAMPLE I

Figure 5:
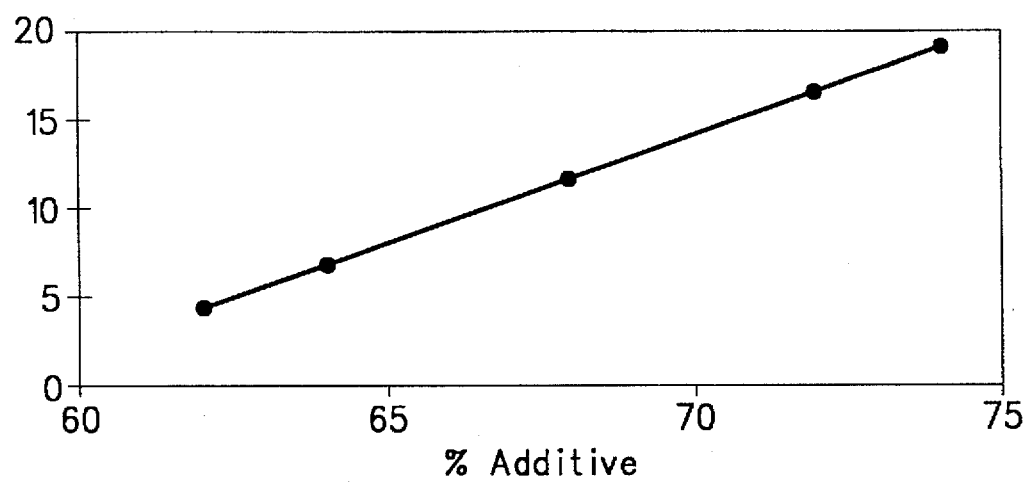
FIG. 5 is a graphical representation of the experimental results obtained in Example 1.

The photometer of FIG. 1 was employed using a reference wavelength filter 76 of 520 nm and an analyzing wavelength of 400 nm through filter 82. Detectors 72 and 78, as used in this example, were silicon. Each wavelength filter had a bandwidth of 10 nm. One meter of 500 micrometer core silica-cladded, silica core fibers were used to serve as conduit means 34 and 50. In other words, sensing means 36 was connected by one cable from light source 14, and to lens 52 of detecting means 54 by the other cable leading from sensing means 36. Sensing means 36 had two lens barrels separated by 0.75 mm to hold the liquid sample 46 therewithin. Using analyzing means 92 of FIG. 1 and FIG. 3, the scaling factors on the proportional controller were adjusted. The analog current output from the PID (4–20 MA) was read with a Fluke 97 scopemeter and plotted against the known concentration of additive, as shown in FIG. 5. In this example, an organic liquid additive was analyzed and had an absorption with a peak centered in the UV area of electromagnetic radiation. The additive was measured on the high wavelength side of this UV peak at 400 nm in the blue visible. By doing so, sample dilution was avoided for the much stronger UV peak. Table 1 represents the data obtained. The correlation coefficient was greater than 0.99 for this calibration.

TABLE 1

| % additive | mA output |
|---|---|
| 62 | 4.58 |
| 64 | 6.92 |
| 68 | 12.00 |
| 72 | 16.65 |
| 74 | 19.03 |

What is claimed is:

1. A photometer for measuring electromagnetic radiation properties modified by a sample comprising:
   a. a source of electromagnetic radiation;
   b. sensing means for transmitting the electromagnetic radiation from said source through the sample to produce an electromagnetic signal;
   c. fiber optic conduit means for directing electromagnetic radiation from said source to said sensing means;
   d. detecting means for converting said electromagnetic signal to an electrical signal at multiple wavelengths, said detecting means including a first beam splitter receiving said electromagnetic signal and outputting first and second electromagnetic beams, each of said first and second beams possessing all wavelengths of the electromagnetic radiation from said source, a second beam splitter receiving said second beam from said first beam splitter and outputting third and fourth electromagnetic beams, each of said third and fourth beams possessing all wavelengths of the electromagnetic radiation, a first detector having a first wavelength filter, a second detector having a second wavelength filter, a third detector having a third wave length filter, said first detector receiving said first beam from said beam splitter, said second detector receiving said third beam from said second beam splitter, said fourth beam from said second beam splitter passing to said third detector, said first, second, and third detectors, each producing an output signal; and
   e. analyzing means for receiving said output signals of said first, second, and third detectors and quantifying the same into data representing a property of the sample, said analyzing means further comprising means for generating a reference signal, selectively, from the output signals of said first, second, and third detectors, said reference signal being compared to said non-reference signals of said first, second, and third detectors.

2. The photometer of claim 1 in which said first, second, and third wavelengths filters of said first, second, and third detectors, respectively, each pass electromagnetic radiation of different wavelengths from one another.

3. The photometer of claim 1 which additionally comprises stabilizing means for maintaining predetermined intensity of said source electromagnetic radiation.

4. The photometer of claim 1 in which said means for generating a reference signal comprises said first electromagnetic beam outputted by said first beam splitter, and said analyzing means includes circuit means for processing a reference signal with said output signal of said first detector.

5. The photometer of claim 1 in which said means for generating a reference signal comprises said third electromagnetic beam outputted by said second beam splitter, and said analyzing means includes circuit means for processing a reference signal with said output signal of said second detector.

6. The photometer of claim 1 which additionally comprises a lens for collimating electromagnetic radiation passed from said sensing means, said collimated electromagnetic being received by said first beam splitter.

7. The photometer of claim 1 which additionally includes first lens associated with said first detector, a second lens associated with said second detector, a third lens associated with said third detector.

8. The photometer of claim 1 in which said conduit means is a first conduit means and which further comprises second conduit means for direction electromagnetic radiation from said sensing means to said detecting means.

9. The photometer of claim 1 which further comprises thermostat means for maintaining a predetermined temperature range of said detection means.

10. The photometer of claim 1 in which said means for generating a reference signal comprises said fourth beam outputted by said second beam splitter, and said analyzing means includes circuit means for processing a reference signal with said output signal of said third detector.

11. A photometer for measuring electromagnetic radiation modified by a sample, comprising:
   a. source of electromagnetic radiation;
   b. sensing means for transmitting the electromagnetic radiation from said source through the sample to produce an electromagnetic signal;
   c. fiber optic conduit means for directing electromagnetic radiation from said source to said sensing means;
   d. detecting means for converting said electromagnetic signal to an electrical signal at multiple wavelengths, said detecting means including a beam splitter receiving said electromagnetic signal and outputting first and second electromagnetic beams, each of said beams possessing all wavelengths of the electromagnetic radiation from said source, a first detector having a first wavelength filter, and a second detector having a second wavelength filter said first detector receiving said first beam, said second detector receiving said second beam, said first and second detectors each producing an output signal; and
   e. analyzing means for receiving said output signals of said first and second detectors and quantifying the same into data representing a property of the sample, said analyzing means further comprising means for generating a reference signal selectively from the output signals of said first and second detectors, said reference signal being compared to said non-reference signal of said first and second detectors.

* * * * *